(12) United States Patent
Schiller et al.

(10) Patent No.: US 8,285,408 B2
(45) Date of Patent: Oct. 9, 2012

(54) SYSTEM AND METHOD FOR DESIGNING AN EAR INSERT DEVICE

(75) Inventors: Ean H. Schiller, Christiansburg, VA (US); William R. Saunders, Backsburg, VA (US)

(73) Assignee: Adaptive Technologies Inc., Blacksburg, VA (US)

( * ) Notice: Subject to any disclaimer, the term of this patent is extended or adjusted under 35 U.S.C. 154(b) by 513 days.

(21) Appl. No.: 12/484,488

(22) Filed: Jun. 15, 2009

(65) Prior Publication Data

US 2010/0318208 A1    Dec. 16, 2010

(51) Int. Cl.
*G06F 19/00* (2011.01)

(52) U.S. Cl. .......... 700/98; 700/118; 700/163; 345/419; 703/2; 381/312

(58) Field of Classification Search .............. 700/98, 700/118, 163; 345/419–420; 703/2; 381/328
See application file for complete search history.

(56) References Cited

U.S. PATENT DOCUMENTS

| | | | | |
|---|---|---|---|---|
| 6,920,414 | B2 * | 7/2005 | Tøpholm | 703/1 |
| 7,447,556 | B2 * | 11/2008 | McBagonluri et al. | 700/98 |
| 7,694,418 | B2 * | 4/2010 | Tøpholm | 29/896.21 |
| 7,801,708 | B2 * | 9/2010 | Unal et al. | 703/2 |
| 7,949,145 | B2 * | 5/2011 | Bachler et al. | 381/322 |
| 7,991,594 | B2 * | 8/2011 | Unal et al. | 703/2 |
| 2004/0165740 | A1 * | 8/2004 | Fang et al. | 381/312 |
| 2005/0088435 | A1 * | 4/2005 | Geng | 345/419 |

* cited by examiner

*Primary Examiner* — John R. Cottingham
*Assistant Examiner* — Douglas Lee
(74) *Attorney, Agent, or Firm* — The Marbury Law Group, PLLC

(57) ABSTRACT

A method for designing an ear insert device using anatomical information relating to the ear. A user record is that includes anatomical information relating to an ear of a user is received. The anatomical information comprises at least one sub-dermal feature of an ear canal. The user record is processed to obtain an ear insert device design record. The ear insert device design record comprises a three dimensional representation of a bounding surface shape having surface boundaries that substantially conform to surface boundaries of the ear canal and the at least one sub-dermal feature of the ear canal. An ear insert device may be produced using the ear insert design record.

41 Claims, 4 Drawing Sheets

SYSTEM AND METHOD FOR DESIGNING AN EAR INSERT DEVICE

BACKGROUND

A significant challenge to fielding custom earplugs is the process for measuring the ears of each user. Like getting measured for custom fitting clothing, customers have to be measured for custom fitting earplugs. That measurement is traditionally accomplished by taking a physical ear impression.

The process of taking a physical ear impression involves injecting a liquid silicone material into the ear to completely fill the ear canal. The liquid silicone flows into and conforms to the exact shape of the ear canal before curing into a flexible solid part. Once fully cured, the solid part is removed from the ear and termed the ear impression. Because it was formed in direct contact with the skin, the surface of the ear impression shows the exact contours of the skin of the ear canal.

The traditional process for earplug fabrication is initiated directly from the physical ear impression. Skilled craftspersons trim and apply wax directly to the silicone ear impression to form it into to the desired earplug shape. Next, the modified impression serves as a master from which a new mold is built and the earplug product is cast from that mold. Newly minted earplug products are later hand-ground and polished to get their final shape. This process is manual labor intensive and difficult to control precisely since each operation is completed by hand working directly on the original record of the ear's shape, the ear impression. If there are any mistakes those errors are difficult to identify and correct because one cannot readily compare the final resulting earplug to the original unmodified ear impression. Also, if there are major mistakes, such as inadvertently trimming away too much of the original ear impression, the process has to be started over.

In recent years industry leaders have developed methods for fabricating custom earplugs using digital manufacturing processes. Most digital processes have used laser scanning equipment to create a digital map of the ear impression surface (a "digital earshape"). Since the impression surface matches the ear surface, a digital earshape is a record of the shape of the ear and serves as the basis for subsequent production operations. The digital earshape can be manipulated using various computerized software tools to form the earplug shape which is then rendered into a physical object through a combination of computer controlled rapid prototyping techniques and injection molding operations.

Physical ear impressions do not provide information about anatomical features below the surface of the ear canal skin (sub-dermal features) such as the thickness of soft tissues or the precise locations along the ear canal that are backed by inflexible bone. Since the ear impression is simply a cast made using the ear canal as a mold, the ear impression cannot reveal anatomical information beyond the characteristics of the skin with which it was in contact while it cured. Below-surface information in not available from the cast of a surface feature or from a scan of such a cast.

A typical earplug manufacturing process utilizes data acquire from physical ear impressions. However, because physical ear impressions do not provide anatomical information, the earplug manufacturing process cannot utilize anatomical information relating to sub-dermal structures within the ear, as for example, the precise location of the temporal bone and the thickness of soft tissue layers, on a user specific basis as a parameter in determining the shape of a hearing protector earplug.

Although some current processes claim to build hearing aids that fit to the "bony part" of the ear, these processes assume the bony part to be the region at, around, or deeper than the "second bend." The qualitative terms "first bend" and "second bend" are common in the ear insert industry. Although it is widely held and qualitatively true that the ear canal enters the temporal bone near the ear canal's second bend, there has not been a precise means of defining or identifying the second bend or defining where the bony part begins relative to that second bend across individuals. For building high-performance ear insert devices, knowing only the qualitative approximate location of the bony part is insufficient and may result in ear insert devices that are too long or too large near the bone and are therefore too uncomfortable to wear. Similarly, ear insert devices built conservatively to stay clear of the second bend may not perform at acceptable levels.

SUMMARY

Embodiments herein provide methods and apparatuses for acquiring data that can be used to derive user-specific anatomical information about the ear. The anatomical information may be used to identify sub-dermal features of the ear canal and/or to precisely locate the bony region of the ear on a user specific basis. Other embodiments provide methods for using this information to determine the shape of an ear insert device.

As used herein, the term "scanning device" encompasses at least a volume computed tomography (VCT) scanner, optical coherence tomography (OCT) scanner, a computed tomography (CT) scanner, a cone beam computed tomography (CBCT) scanner, a positron emission tomography (PET) scanner, a magnetic resonance (MR) scanner, an ultrasound scanner, an optical scanner, or a laser scanner.

As used herein, the term "anatomical information" as it relates to the ear encompasses surface features, dimensional metrics and sub-dermal features of the ear canal. By way of illustration and not as a limitation, anatomical information may include information relating to the dimensions and shape of the ear canal, the location and position of the boney region, the surface features of the ear canal, the location and position of the eardrum, the location and position of the jaw bone, the location and position of other sub-dermal features, and tissue thicknesses of the ear canal, the bounding surfaces of the ear canal, and the external acoustic meatus (ear canal) from the aperture in the concha to the bony part (where ear canal enters the temporal bone). By way of illustration and not by way of limitation, sub-dermal anatomical features may include the most proximal surfaces of the tympanic part of the temporal bone (part of skull through/into which the ear canal passes) and/or the Condyloid process of the mandible (posterior articular surface of the jaw bone).

As used herein the term "ear insert device" encompasses a device inserted into the ear for hearing protection, hearing enhancement, communications, audio playback, wireless or connected communication devices (headsets, mobile phones, personal agents), loud speakers, tinnitus masking devices, devices recording vibrations in the ear canal and transforming these into audio signals, voice recognition devices, earplugs, noise blockers with selective frequencies or sound levels, Man Machine Interface (MMI) products that enable clear communication even in the noisiest environments, or products related to wireless Internet applications. The ear insert device may be a passive device or may comprise components that, for example, produce, detect and/or condition audio signals.

DETAILED DESCRIPTION

Embodiments herein provide methods and apparatuses for acquiring data that can be used to derive user-specific anatomical information about the ear. cThe anatomical information may be used to identify sub-dermal features of the ear canal and to locate the bony region of the ear on a user specific basis. Other embodiments provide methods for using this information to determine the shape of an ear insert device and for manufacturing an ear insert device that accommodates anatomical features of the ear.

Figure 1:
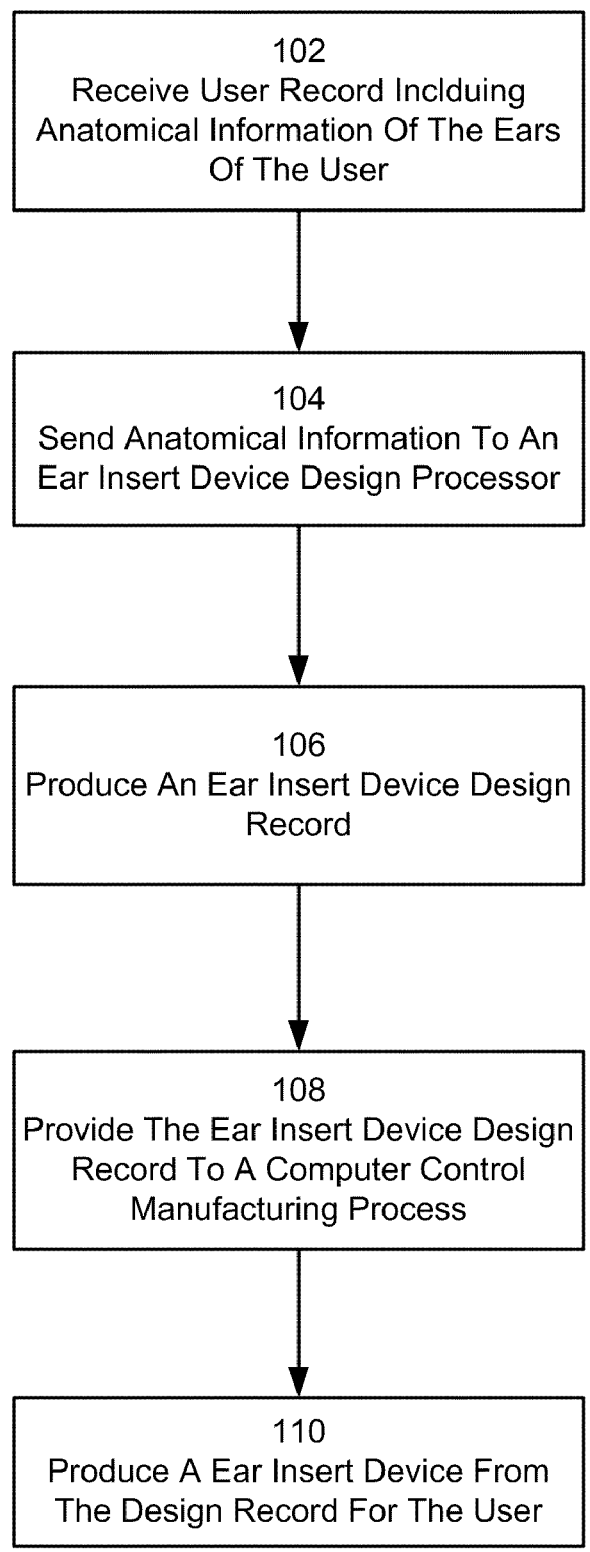
FIG. 1 is a flow diagram illustrating a process to determine the shape of an ear insert device according to an embodiment.

FIG. 1 is a flow diagram illustrating a process to determine the shape of an ear insert device according to an embodiment.

A user record comprising user-specific anatomical information relating to the user's ears is received (block 102). By way of illustration and not by way of limitation the anatomical information may be derived from imaging data acquired using computed tomography (CT), volume computed tomography (VCT), cone beam computed tomography (CBCT), positron emission tomography (PET), optical coherent tomography, magnetic resonance (MR), ultrasound, optical scanning, and laser scanning.

For each ear, the user-specific anatomical information provides three-dimensional representations of the bounding surfaces of the ear canal from the concha to the tympanic membrane and identifies the relative position of the sub-dermal anatomical features. In an embodiment, the sub-dermal anatomical features include the most proximal surfaces of the tympanic part of the temporal bone (part of skull through/into which the ear canal passes) and the Condyloid process of the mandible (posterior articular surface of the jaw bone).

In an embodiment, the user record comprises spatially correlated data representing properties of the specific user's ears and proximal anatomical features. By way of illustration and not by way of limitation, these properties may include geometric, mechanical and chemical measures such as size, shape, position, stiffness, density, radiodensity, fluid content and chemical composition. The proximal anatomical features may include the pinna (also called the auricula), external acoustic meatus (also called the ear canal), tympanic membrane (also called the ear drum), cartilaginous part of external acoustic meatus, cartilage of auricula, temporal bone, mandible and neighboring tissues.

By including for the sub-dermal features of the ear canal, the ear insert device may be designed to account for interferences with sub-dermal anatomical features and to provide clearances from such features. In an embodiment, the clearances and/or interferences may range between 0 and 3 mm in magnitude. In a particular application, the clearance and/or interference may exceed 3 mm. In an embodiment, the ear insert device is designed to deform at one or more locations to accommodate sub-dermal anatomical features. In another embodiment, the ear insert device is designed to deform soft tissue in one or more locations of the ear canal.

The user record is sent to a design processor (block 104). In response to instructions stored in a memory, the design processor generates an ear insert device design record (block 106). In an embodiment, the anatomical information relating to the sub-dermal structures of the ear canal are extracted from the user record. In an embodiment, the ear insert device design record is suitable for use in a computer controlled manufacturing process to produce for each ear an ear insert device that is shaped to conform to the bounding surfaces of the ear canal and the sub-dermal anatomical features of the ear canal.

In another embodiment, the ear insert device design record may be used in conjunction with specific fitment goals to arrive at a final design of the ear insert device. By way of illustration and not by way of limitation, the size, shape and material of the ear insert device may be selected to achieve a level of compression of the soft tissue of the ear canal. The size, shape and material of the ear insert device may be also selected to create interferences with and/or clearances from portions of the ear and/or sub-dermal anatomical features.

In an embodiment, a sub-dermal feature is a bony aperture in the temporal bone that is generally associated with the second bend of the ear canal. In this embodiment, the boney aperture may be identified using individually specific anatomical data to include the surface shape of the temporal bone. Locations along the ear canal nearer to the ear drum (tympanic membrane) are lined with very thin tissue backed by rigid bone whereas locations along the ear canal farther from the ear drum are backed by a substantially thicker layer of tissue between the ear canal surface and any surrounding bone, if present.

In an embodiment, the tip of an ear insert device may be cut or shaped relative to the location of the boney aperture. The tip may be terminated before, at or after the boney aperture. The shape of the tip of the ear insert device may be selected based on the termination point of the tip and/or desired performance parameters.

The user record may be received by the processor via a network or from transportable storage media. The ear insert device design record may be delivered to a computer controlled manufacturing system via a network or by transportable storage media.

The ear insert device design record may be provided to a computer control manufacturing process (block 108). Using the ear insert device design record, the computer controlled manufacturing process may then produce an ear insert device for the user (block 110). In an embodiment, the computer controlled manufacturing process uses injection molding to produce an ear insert device. The ear insert device may use resilient polymeric material. By way of illustration and not by way of limitation, the polymeric material may have a Shore A durometer in the range of 20 to 90.

In an embodiment, the ear insert device may be a device inserted into the ear for hearing protection, hearing enhancement, communications, audio playback, and wireless or connected communication devices (headsets, mobile phones, personal agents), loud speakers, tinnitus masking devices, devices recording vibrations in the skull and transforming these into audio signals, voice recognition devices, earplugs, noise blockers with selective frequencies or sound levels, Man Machine Interface (MMI) products and devices related to wireless Internet applications.

The ear insert device may incorporate active and passive components to convey, amplify, suppress and filter audio signals originating from inside or outside the ear. The ear insert device may also incorporate components to interface with radio frequency or other communications devices so as to receive non-audio communications, to produce audio signals from such non-audio communications and to convey such audio signals to the user. The ear insert device may also incorporate components to interface with devices external to the ear.

Figure 2:
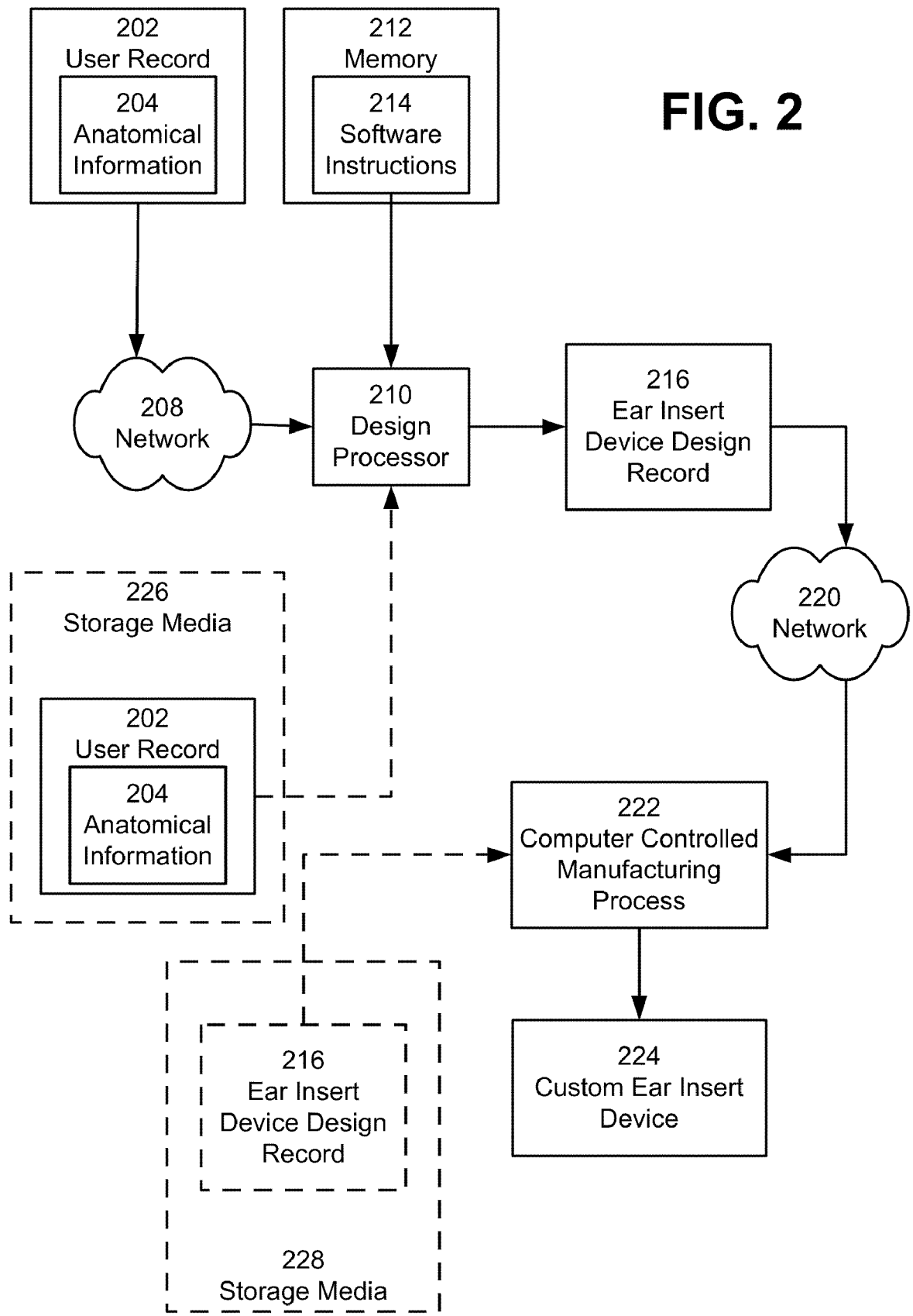
FIG. 2 is a block diagram illustrating components of a system for designing and fabricating an ear insert device.

FIG. 2 is a block diagram illustrating components of a system for designing and fabricating an ear insert device.

A user record 202 comprising user-specific anatomical information relating to the user's ears is received. By way of illustration and not by way of limitation the anatomical information may be derived from data acquired using computed tomography (CT), volume computed tomography (VCT), cone beam computed tomography (CBCT), positron emission tomography (PET), optical coherent tomography, magnetic resonance (MR), ultrasound, optical scanning, laser scanning and collection of physical ear impressions or casts.

For each ear, the user-specific anatomical information provides three-dimensional representations of the bounding surfaces of the ear canal from the concha to the temporal membrane and identifies the relative position of the sub-dermal anatomical features. In an embodiment, the sub-dermal anatomical features include the most proximal surfaces of the tympanic part of the temporal bone (part of skull through/into which the ear canal passes) and the Condyloid process of the mandible (posterior articular surface of the jaw bone).

In an embodiment, the user record comprises spatially correlated data representing properties of the specific user's ears and proximal anatomical features. By way of illustration and not by way of limitation, these properties may include geometric, mechanical and chemical measures such as size, shape, position, stiffness, density, radiodensity, fluid content and chemical composition. The proximal anatomical features may include the pinna (also called the auricula), external acoustic meatus (also called the ear canal), tympanic membrane (also called the ear drum), cartilaginous part of external acoustic meatus, cartilage of auricula, temporal bone, mandible and neighboring tissues.

By including for the sub-dermal features of the ear canal, the ear insert device may be designed to account for interferences with sub-dermal anatomical features and to provide clearances from such features. Typically, the clearances range between 0 and 3 mm in magnitude.

The user record is sent to a design processor 210. In response to instructions 214 stored in a memory 212, the design processor 210 generates an ear insert device design record 216. In an embodiment, the anatomical information relating to the sub-dermal structures of the ear canal are extracted from the user record. In an embodiment, the ear insert device design record is suitable for use in a computer controlled manufacturing process to produce for each ear an ear insert device that is shaped to conform to the bounding surfaces of the ear canal and the sub-dermal anatomical features of the ear canal. In another embodiment, the ear insert device design record may be used in conjunction with specific fitment goals to arrive at a final design of the ear insert device. By way of illustration and not by way of limitation, the size, shape and material of the ear insert device may be selected to achieve a level of compression of the soft tissue of the ear canal. The size, shape and material of the ear insert device may be also selected to create interferences with and/or clearances from portions of the ear and/or sub-dermal anatomical features.

The user record 202 may be received by the processor via a network 208 or from transportable storage media 226. The ear insert device design record may be ear insert device design record may be delivered to a computer controlled manufacturing system via a network 220 or by transportable storage media 228.

The ear insert device design record may be provided to a computer control manufacturing process 222. Using the ear insert device design record 216, the computer controlled manufacturing process 222 may then produce an ear insert device for the user 224. In an embodiment, the computer controlled manufacturing process 222 uses injection molding to produce an ear insert device 224. The ear insert device 224 may use resilient polymetric material. By way of illustration and not by way of limitation, the polymetric material may have a Shore A durometer in the range of 20 to 90.

In an embodiment, the ear insert device 224 may be a device inserted into the ear for hearing protection, hearing enhancement, communications, audio playback, and wireless or connected communication devices (headsets, mobile phones, personal agents), loud speakers, tinnitus masking devices, devices recording vibrations in the ear canal and transforming these into audio signals, voice recognition devices, earplugs, noise blockers with selective frequencies or sound levels, dosimetry devices, Man Machine Interface (MMI) products and devices related to wireless Internet applications.

The ear insert device may incorporate active and passive components to convey, amplify, suppress and filter audio signals originating from outside the ear. The ear insert device may also incorporate components to interface with radio frequency or other communications devices so as to receive non-audio communications, to produce audio signals from such non-audio communications and to convey such audio signals to the user. The ear insert device may also incorporate components to interface with devices external to the ear.

In an embodiment, a VCT scanner is configured to acquire imaging data from the ears of a user. The configuration of the scanner encompasses setting of the radiation dose and the positioning and movement of the scanner head. In another embodiment, the positioning and movement of the VCT scanner head and the radiation dose are controlled by a controller processor in response to instructions stored in a memory. The instructions may define a protocol in which the positioning and movement of the VCT scanner head, radiation output and/or duration of a scan are controlled automatically.

In still another embodiment, the field of view of a VCT scanner is extended. The extended view VCT scanner is used with a protocol that causes the controller to operate the VCT scanner so as to acquire anatomical data from both ears in a single sequence. Obtaining a scan of both ears in a single sequence is advantageous to provide images that depict relationships between the structures of the ears and that are less prone to errors that may be introduced by performing scans of the left and right ears sequentially and to further minimize the radiation exposure to the individual being scanned.

By way of illustration and not by way of limitation, protocols for two VCT scanners made by Xoran Technologies Inc., the MiniCAT™ and the xCAT® ENT, have been adapted to acquire imaging data usable to produce the user record described above. In one series of tests, a MiniCAT was operated using a first sinus protocol that produced a 600 projection frames scan over 40 seconds using mode 1 and a second sinus protocol that produced 300 projection frames scan over 20 seconds using mode 3. In another test, an xCat was operated using a 40 second full head scan protocol of a single subject to provide a scan of both ears.

The anatomical information from the user record may be provided to a design processor that in response to instructions stored in a memory generates an ear insert device design record. In an embodiment, the ear insert device design record is suitable for use in a computer controlled manufacturing process to produce for each ear an ear insert device that is shaped to conform to the bounding surfaces of the ear canal and the sub-dermal anatomical features of the ear canal.

By way of illustration and not by way of limitation, in an embodiment, the VCT datasets generated by the scanner comprise a series of 2D slices called a stack. Each slice is effectively an x-ray image revealing a different, very thin, cross section of the user's head. To extract the earshape, the air space within the earcanal is isolated from the surrounding tissue and bone using an image processing routine. The processing routine alters the distribution of pixel values for each slice in the stack. XY-coordinates of each outline pixel are determinate and are assigned an elevation (Z-value) according to the slice's position in the stack and the thickness of tissue represented by each slice. For example, for slice 100 having a slice thickness of 0.2 Z=20 mm to yield XYZ-coordinates which are fully defined in 3D space. The collection of outline points from all of the slices forms a 3D point cloud of the earshape.

In this embodiment, the point cloud is further processed to remove outliers and disconnected components such as small air-pockets in the temporal bone which may have been outlined during image processing. Noise reduction and smoothing operations are applied to further refine the point cloud prior to surface meshing. Meshing forms triangular elements between adjacent points of the point cloud to fill-in the surface of the earshape.

To make the VCT-based earshape output compatible with current digital production needs, the orientation of final shape and the number of triangles used to represent the surface is adjusted to match that typical of laser scanner output.

In an embodiment, a scanner having a field of view large enough to measure both ears at once is used to obtain the anatomical data. In an embodiment, a scanner is configured to obtain anatomical features to a resolution of 0.2 mm or better.

In an embodiment, the raw scanner output (e.g., the imaging data) may be transmitted electronically for processing. In this context, "processing" may include the extraction of sub-dermal anatomical data from the images.

In another embodiment, the ear insert device design record may be used in conjunction with specific fitment goals to arrive at a final design of the ear insert device. By way of illustration and not by way of limitation, the size, shape and material of the ear insert device may be selected to achieve a level of compression of the soft tissue of the ear canal. The size, shape and material of the ear insert device may be also selected to create interferences with and/or clearances from portions of the ear and/or sub-dermal anatomical features. In still another embodiment, the file is processed to be compatible with a file format produced by scanning a physical ear impression. That digital earshape file may be sent electronically to a hearing instrument manufacturer for production of an ear insert device.

As previously noted, an ear insert device may further comprise electronic components to, for example, convey audio signals into the ear canal, to detect audio signals inside the ear canal, and to condition audio signals within the ear canal. In other embodiments, an ear insert device may utilize components to perform these and other functions using the boney structures of the ear.

Figure 3:
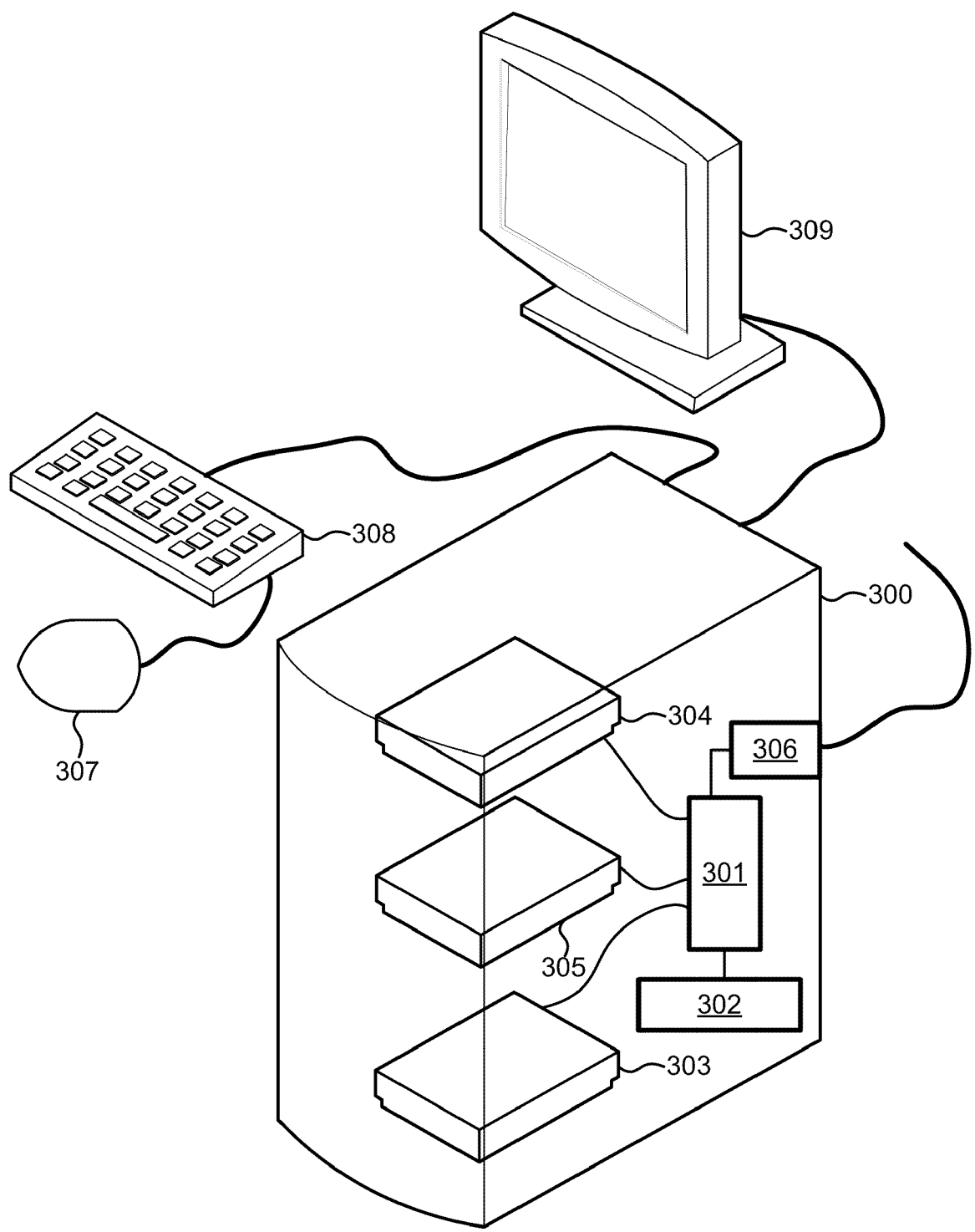
FIG. 3 is a component block diagram of a personal computer suitable for use in the various embodiments.

The embodiments described above may also be implemented on any of a variety of computers, such as a personal computer 300 illustrated in FIG. 3. Such a personal computer 300 typically includes a processor 301 coupled to volatile memory 302 and a large capacity nonvolatile memory, such as a disk drive 303. The computer 300 may also include a floppy disc drive 304 and a compact disc (CD) drive 305 coupled to the processor 301. Typically the computer 300 will also include a pointing device such as a mouse 307, a user input device such as a keyboard 308 and a display 309. The computer 300 may also include a number of network connection circuits 306, such as a USB or FireWire®, coupled to the processor 301 for establishing data connections to external devices such as a programmable device being tested. In a notebook configuration, the computer housing includes the pointing device 307, keyboard 308 and the display 309 as is well known in the computer arts.

Figure 4:
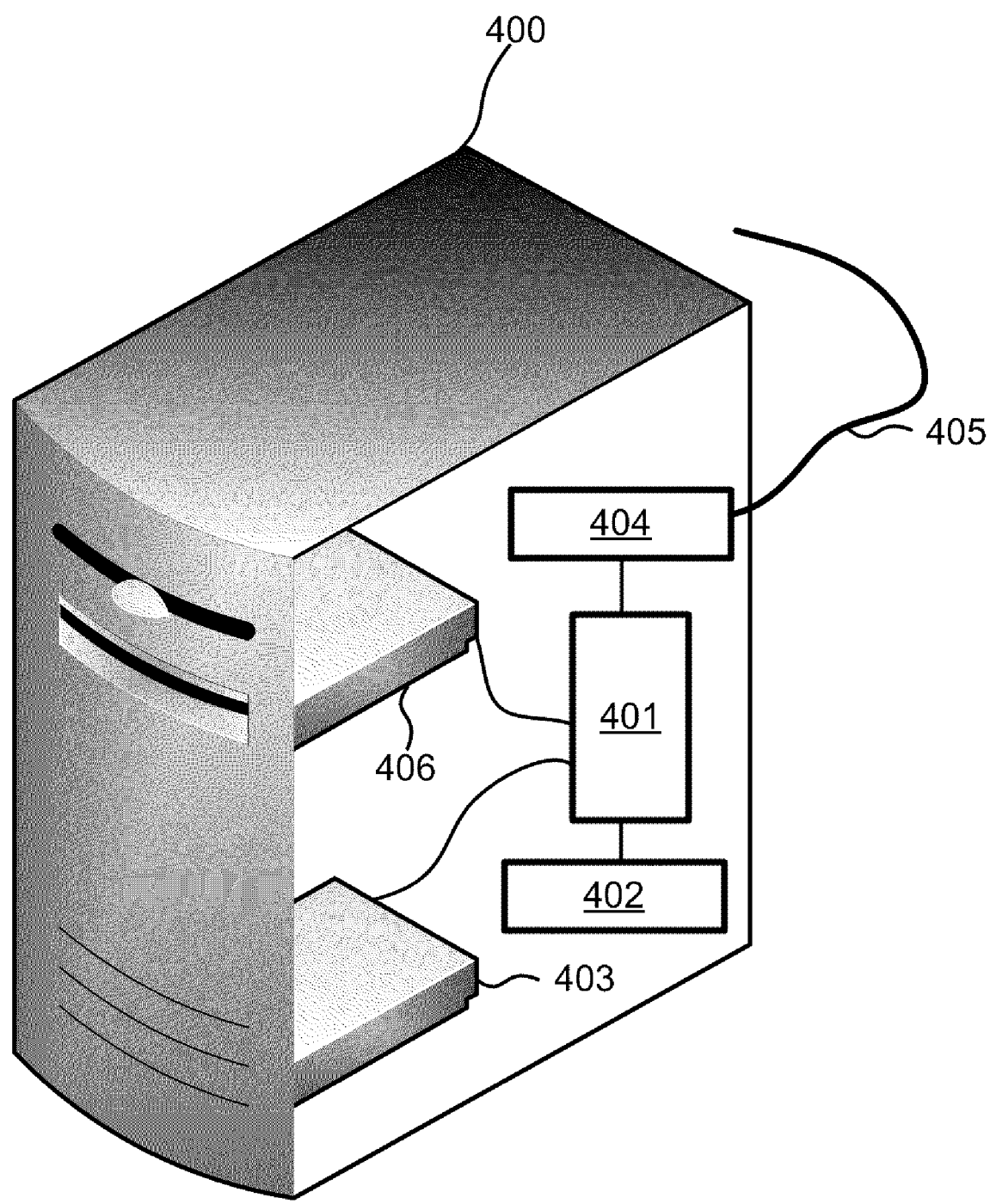
FIG. 4 is a component block diagram of a server device suitable for use in the various embodiments.

A number of the aspects described above may also be implemented with any of a variety of remote server devices, such as the server 400 illustrated in FIG. 4. Such a server 400 typically includes a processor 401 coupled to volatile memory 402 and a large capacity nonvolatile memory, such as a disk drive 403. The server 400 may also include a floppy disc drive and/or a compact disc (CD) drive 406 coupled to the processor 401. The server 400 may also include a number of connector ports 404 coupled to the processor 401 for establishing data connections with network circuits 405.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module executed which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the following claims and the principles and novel features disclosed herein

What is claimed is:

1. A method for designing an ear insert device comprising:
   receiving by a processor a user record, wherein the user record comprises anatomical information relating to an ear of a user and wherein the anatomical information comprises three dimensional measurement data of at least one sub-dermal feature of an ear canal; and
   processing by the processor the user record to obtain an ear insert device design record, wherein the ear insert device design record comprises a three dimensional representation of a bounding surface shape having surface boundaries that substantially conform to surface boundaries of the ear canal and the at least one sub-dermal feature of the ear canal.

2. The method of claim 1 further comprising using the ear insert device design record to produce an ear insert device that substantially conforms to the surface boundaries of the ear canal and the at least one sub-dermal feature of the ear canal.

3. The method of claim 2, wherein the ear insert device comprises a distal end and wherein using the ear insert device design record to produce an ear insert device comprises using the ear insert device design record to produce an ear insert device having the distal end terminated relative to the at least one sub-dermal anatomical feature of the ear canal.

4. The method of claim 2, wherein the ear insert device comprises a distal end and wherein using the ear insert device design record to produce an ear insert device comprises using the ear insert device design record to produce an ear insert device having the distal end shaped to accommodate the at least one sub-dermal feature of the ear canal.

5. The method of claim 1, wherein the at least one sub-dermal feature is selected from the group consisting of a most proximal surface of the tympanic part of the temporal bone, a soft tissue of the ear canal, and a Condyloid process of the mandible.

6. The method of claim 2, wherein using the ear insert device design record to produce an ear insert device that substantially conforms to the surface boundaries of the ear canal and the at least one sub-dermal feature of the ear canal comprises using the ear insert device design record to produce an ear insert device that when inserted into the ear canal clears the at least one sub-dermal feature by about 0 to about 3 millimeters.

7. The method of claim 2, wherein using the ear insert device design record to produce an ear insert device that substantially conforms to the surface boundaries of the ear canal and the at least one sub-dermal feature of the ear canal comprises using the ear insert device design record to produce an ear insert device that when inserted in the ear canal deforms the ear insert device by about 0 to about 3 millimeters.

8. The method of claim 2, wherein using the ear insert device design record to produce an ear insert device that substantially conforms to the surface boundaries of the ear canal and the at least one sub-dermal feature of the ear canal comprises using the ear insert device design record to produce an ear insert device that when inserted in the ear canal deforms a soft tissue of the ear canal by about 0 to about 3 millimeters.

9. The method of claim 1, wherein the anatomical information comprises spatially correlated data representing properties of the ear canal and the at least one sub-dermal feature.

10. The method of claim 9, wherein the properties are selected from the group consisting of a size, shape, position, stiffness, density, radiodensity, fluid content and chemical composition.

11. The method of claim 1, wherein the at least one sub-dermal feature is selected from the group consisting of a pinna, a tissue associated with the pinna, an ear canal, a tissue associated with the ear canal, a tympanic membrane, a tissue associated with the tympanic membrane, a cartilaginous part of external acoustic meatus, a tissue associated with the cartilaginous part of external acoustic meatus, a cartilage of auricula, a tissue associated with the cartilage of auricular, a temporal bone, a tissue associated with the temporal bone, a mandible and a tissue associated with the mandible.

12. The method of claim 1 further comprising:
   acquiring imaging data using a collection device selected from the group consisting of a computed tomography (CT) scanner, a volume computed tomography (VCT) scanner, a cone beam computed tomography (CBCT) scanner, a positron emission tomography (PET) scanner, an optical coherent tomography scanner, a magnetic resonance (MR) scanner, an ultrasound scanner, an optical scanner, a laser scanner;
   extracting from the imaging data the anatomical information; and
   storing the anatomical information in the user record.

13. The method of claim 1, wherein the user record is stored in a datastore accessible via a network and wherein receiving the user record comprises receiving the user record from the datastore via the network.

14. The method of claim 2, wherein using the ear insert device design record to produce an ear insert device comprises using the ear insert device design record to control a computer controlled manufacturing process.

15. The method of claim 2, wherein using the ear insert device design record to produce an ear insert device comprises using the ear insert device design record to form an injection mold and using the injection mold to produce the ear insert device.

16. The method of claim 2, wherein the ear insert device is selected from the group consisting of a device inserted into the ear for hearing protection, hearing enhancement, communications, audio playback, wireless communications, wired communications, tinnitus masking, noise blocking, selective audio frequency filtering, and selective audio frequency enhancement.

17. The method of claim 2, wherein the ear insert device is composed of a resilient polymeric material with a durometer of between about 20 and 90 on the Shore A scale.

18. The method of claim 2, wherein using the ear insert device design record to produce an ear insert device comprises using the ear insert device design record to select materials for fabrication of the ear insert device and wherein the method further comprises selecting a first fabrication material for portions of the ear insert device that substantially conforms to the surface boundaries of the ear canal and selecting a second fabrication material that substantially conforms to the at least one sub-dermal feature of the ear canal.

19. The method of claim 18, wherein the at least one sub-dermal feature of the ear canal comprises a level of compression of a fleshly layer of the ear canal.

20. The method of claim 1, wherein processing the user record to obtain an ear insert device design record comprises converting the user record to a format recognized by a computer controlled manufacturing process.

21. A system for designing an ear insert device comprising:
a user record, wherein the user record comprises anatomical information relating to an ear of a user and wherein the anatomical information comprises three dimensional measurement data of at least one sub-dermal feature of an ear canal;
a design processor, wherein the design processor is configured with software executable instructions to cause the design processor to perform operations comprising processing the user record to obtain a ear insert device design record, wherein the ear insert device design record comprises a three dimensional representation of a bounding surface shape having surface boundaries that substantially conform to surface boundaries of the ear canal and the at least one sub-dermal features of the ear canal.

22. The system of claim 21 further comprising a production server, wherein the production server is configured with software executable instructions to cause the production server to perform operations comprising using the ear insert device design record to produce an ear insert device that substantially conforms to the surface boundaries of the ear canal and the at least one sub-dermal feature of the ear canal.

23. The system of claim 22, wherein the ear insert device comprises a distal end wherein the instruction for using the ear insert device design record to produce an ear insert device comprises an instruction for using the ear insert device design record to produce an ear insert device having the distal end terminated relative to the at least one sub-dermal feature of the ear canal.

24. The system of claim 22, wherein the ear insert device comprises a distal end wherein the instruction for using the ear insert device design record to produce an ear insert device comprises an instruction for using the ear insert device design record to produce an ear insert device having the distal end shaped to accommodate the at least one sub-dermal feature of the ear canal.

25. The system of claim 21, wherein the at least one sub-dermal feature is selected from the group consisting of a most proximal surface of the tympanic part of the temporal bone, a soft tissue of the ear canal, and a Condyloid process of the mandible.

26. The system of claim 22, wherein the instruction for using the ear insert device design record to produce an ear insert device that substantially conforms to the surface boundaries of the ear canal and the at least one sub-dermal feature of the ear canal comprises an instruction for using the ear insert device design record to produce an ear insert device that when inserted in the ear canal clears the at least one sub-dermal feature by 0 to about 3 millimeters.

27. The system of claim 22, wherein the instruction for using the ear insert device design record to produce an ear insert device that substantially conforms to the surface boundaries of the ear canal and the at least one sub-dermal feature of the ear canal comprises an instruction for using the ear insert device design record to produce an ear insert device that when inserted into the ear canal clears the at least one sub-dermal feature by from 0 to about 3 millimeters.

28. The system of claim 22, wherein the instruction for using the ear insert device design record to produce an ear insert device that conforms to the surface boundaries of the ear canal and the at least one sub-dermal feature of the ear canal comprises an instruction for using the ear insert device design record to produce an ear insert device that when inserted in the ear canal clears the at least one sub-dermal feature by 0 to about 3 millimeters.

29. The system of claim 21, wherein the anatomical information comprises spatially correlated data representing properties of the ear canal and the at least one feature.

30. The system of claim 29, wherein the properties are selected from the group consisting of a size, shape, position, stiffness, density, radiodensity, fluid content and chemical composition.

31. The system of claim 21, wherein the at least one feature is selected from the group consisting of a pinna, a tissue associated with the pinna, an ear canal, a tissue associated with the ear canal, a tympanic membrane, a tissue associated with the tympanic membrane, a cartilaginous part of external acoustic meatus, a tissue associated with the cartilaginous part of external acoustic meatus, a cartilage of auricula, a tissue associated with the cartilage of auricular, a temporal bone, a tissue associated with the temporal bone, a mandible and a tissue associated with the manible.

32. The system of claim 21, wherein the anatomical information is extracted from imaging data generated using a collection device selected from the group consisting of a computed tomography (CT) scanner, a volume computed tomography (VCT) scanner, a cone beam computed tomography (CBCT) scanner, a positron emission tomography (PET) scanner, an optical coherent tomography scanner, a magnetic resonance (MR) scanner, an ultrasound scanner, an optical scanner, a laser scanner.

33. The system of claim 21 further comprising a datastore and a network, wherein the user record is stored in the datastore accessible to the design processor via the network and the instruction for receiving the user record comprises an instruction for receiving the user record from the datastore via the network.

34. The system of claim 22, wherein the instruction for using the ear insert device design record to produce an ear insert device comprises an instruction for using the ear insert device design record to control a computer controlled manufacturing process.

35. The system of claim 22, wherein the instruction for using the ear insert device design record to produce an ear insert device comprises an instruction for using the ear insert device design record to form an injection mold and using the injection mold to produce the ear insert device.

36. The system of claim 22, wherein the ear insert device is selected from the group consisting of a device inserted into the ear for hearing protection, hearing enhancement, communications, audio playback, wireless communications, wired communications, tinnitus masking, noise blocking, selective audio frequency filtering, and selective audio frequency enhancement.

37. The system of claim 22, wherein the ear insert device is composed of a resilient polymeric material with a durometer of between about 20 and 90 on the Shore A scale.

38. The system of claim 22, wherein the instruction for using the ear insert device design record to produce an ear insert device comprises an instruction for using the ear insert device design record to select materials for fabrication of the ear insert device and wherein the design processor is further configured with software executable instructions that cause the design process to perform the operation of selecting a first fabrication material for portions of the ear insert device that substantially conforms to the surface boundaries of the ear canal and selecting a second fabrication material that substantially conforms to the at least one sub-dermal feature of the ear canal.

39. The system of claim 38, wherein the at least one sub-dermal feature of the ear canal comprises a level of compression of a fleshly layer of the ear canal.

40. The system of claim 21, wherein the instruction for processing the user record to obtain an ear insert device design record comprises an instruction for converting the user record to a format recognized by a computer controlled manufacturing process.

41. A method for designing an ear insert device comprising:
  receiving by a processor a user record, wherein the user record comprises anatomical information relating to an ear of a user and wherein the anatomical information comprises at least one sub-dermal feature of an ear canal; and
  processing by the processor the user record to obtain an ear insert device design record, wherein the ear insert device design record comprises a three dimensional representation of a bounding surface shape having surface boundaries that substantially conform to surface boundaries of the ear canal and the at least one sub-dermal feature of the ear canal; and
  using by the processor the ear insert device design record to:
    select a first fabrication material;
    select a second fabrication material; and
    produce an ear insert device that substantially conforms to the surface boundaries of the ear canal using the first fabrication material and conforms to the at least one sub-dermal feature of the ear canal using the second fabrication material.

* * * * *

UNITED STATES PATENT AND TRADEMARK OFFICE
CERTIFICATE OF CORRECTION

Page 1 of 1

PATENT NO. : 8,285,408 B2
APPLICATION NO. : 12/484488
DATED : October 9, 2012
INVENTOR(S) : Ean H. Schiller and William R. Saunders It is certified that error appears in the above-identified patent and that said Letters Patent is hereby corrected as shown below:

In the Specification

Col. 1, lines 3-4, before paragraph [0001], please insert:

--This invention was made with Government support under N68335-10-C-0011 awarded by the Department of the Navy. The Government has certain rights in this invention.--

Signed and Sealed this
Fifth Day of August, 2014

Michelle K. Lee
*Deputy Director of the United States Patent and Trademark Office*